(12) United States Patent
Roy

(10) Patent No.: US 6,662,967 B2
(45) Date of Patent: Dec. 16, 2003

(54) BANDAGE DISPENSER

(76) Inventor: Eric R. Roy, 415 Port Royal Blvd., Satellite Beach, FL (US) 32937

( * ) Notice: Subject to any disclaimer, the term of this patent is extended or adjusted under 35 U.S.C. 154(b) by 0 days.

(21) Appl. No.: 10/072,135

(22) Filed: Feb. 7, 2002

(65) Prior Publication Data

US 2002/0162847 A1 Nov. 7, 2002

Related U.S. Application Data

(60) Provisional application No. 60/289,071, filed on May 7, 2001.

(51) Int. Cl.⁷ ................................................. B65H 1/08
(52) U.S. Cl. ......................................... 221/58; 206/441
(58) Field of Search .............................. 221/33, 45, 46, 221/55, 58, 59, 60, 63; 206/441, 445, 812, 440

(56) References Cited

U.S. PATENT DOCUMENTS 1,490,070 A  *  4/1924  Korth ........................... 221/47
5,271,522 A     12/1993  Ko et al.
6,079,190 A      6/2000  Simpson

* cited by examiner

*Primary Examiner*—Kenneth W. Noland
(74) *Attorney, Agent, or Firm*—John L. DeAngelis, Jr.; Beusse Brownlee Bowdoin & Wolter, P.A.

(57) ABSTRACT

A bandage or other injury dressing dispenser is disclosed. The dispenser includes a plurality of differently-sized compartments, one for each injury dressing size. The dispenser includes bottom, front, rear and top surfaces and further includes a tension member in each compartment, for providing a biasing force between the compartment rear surface and a backing plate in each compartment. The injury dressings are disposed vertically between the backing plate and the front compartment surface, such that the tension member urges the injury dressings forwardly against the interior side of the front surface. The injury dressings are dispensed from a slot in the bottom surface of each compartment by the application of a downwardly directed force against the injury dressing through an arcuate opening in the front surface of each compartment.

16 Claims, 13 Drawing Sheets

BANDAGE DISPENSER

This patent application claims the benefit of Provisional Patent Application No. 60/289,071 filed on May 7, 2001.

FIELD OF THE INVENTION

The present invention relates to prepackaged adhesive bandages and in particular relates to an apparatus for conveniently dispensing adhesive bandages.

BACKGROUND OF THE INVENTION

First-aid bandages or strip bandages (also referred to as finger bandages) are well known first-aid devices for covering contusions and abrasions. The conventional bandage comprises an elongated strip of medical grade pressure-sensitive adhesive tape with a centrally disposed absorbent gauze portion, leaving free adhesive material on both sides of the absorbent pad for securing the bandage to the skin over the wound. Typically, prior to use the adhesive portion is covered by a release sheet to avoid premature contact with the adhesive portion. The strip bandages, with the release sheet in place, are conventionally packaged in a sterile paper sleeve, which is ripped open using a pull-thread opening arrangement or by tearing the end section of the enclosure to expose an end of the bandage. The bandage is then removed from the package, the release sheet removed and the bandage applied to the wound.

The conventional bandage strips are marketed and sold in rectangular containers having an upper flap lid that opens to reveal a mixed assortment of packaged bandage strips of various sizes and shapes. This packaging makes it difficult for the user to observe and select the desired bandage strip from the container, as frequently the various bandage sizes and shapes are not separated and therefore become disorganized within the container. It is especially awkward and difficult to locate and grasp the desired bandage size and shape while the user is bleeding and may have an antibiotic ointment applied over the wound. Since all of the bandages are housed within one container, there is a tendency to exhaust the more popular bandage strips, a situation which typically remains unknown to the user until that size bandage strip is needed. The conventional flap type lids may also require a certain headroom distance to open and if not conveniently stored in a fixed location, may be troublesome to locate in an emergency.

U.S. Pat. No. 6,079,190 discloses a bandage package and dispensing apparatus that provides for the dispensing of individual bandages as required. However, this apparatus requires specialized and customized bandage packaging. Conventionally packaged bandages will not properly function within this apparatus.

BRIEF SUMMARY OF THE INVENTION

The present invention is directed to a dispenser in which the bandages strips are segregated into dispensing compartments based on bandage size, and oriented vertically within each compartment. The bandages are conveniently dispensed from each compartment by the user's application of a force through a front-surface opening that exposes a portion of the first bandage stored within the compartment. One or more helical springs (or other force imparting mechanisms) are disposed between the rear interior surface of each compartment and a movable plastic backing member in each compartment, which is approximately the same size as the bandages stored therewithin. Thus the spring urges the backing member against the stack of parallel, vertically-oriented bandages, which in turn urges the bandages against the front surface of the compartment for dispensing through the front-surface opening. In one embodiment, the front-surface opening is formed as an arcuate cut-out area.

The bandages are easily dispensed by the application of a force against the row of bandages through the cut-out area, which force has a component perpendicular to the bandages and is resisted by the opposing spring-directed force. When such a force is supplied by the user's thumb or finger against the first bandage, a sufficient frictional force between the user's thumb and the first bandage is created such that a second downwardly-directed component of the user-applied force allows the user to slidably withdraw the first bandage in the row from a slot located in the bottom surface of the compartment adjacent the cut-out in the front surface. Since the dispenser includes a plurality of different-sized compartments, several bandage sizes can be housed within the dispenser and dispensed from it.

In one embodiment of the invention, individually wrapped gauze pads can also be dispensed from a suitably-sized compartment of the dispenser, in a manner similar to the dispensing of strip bandages.

The dispenser further includes a compartment for holding and dispensing first aid cream or other semi-liquid or viscous medicinal material. In one embodiment, a flexible tube containing, for instance, first aid cream, is placed vertically within a suitably configured compartment of the dispenser, with the tube dispensing orifice facing downwardly and fixed within the bottom surface of the compartment. The user applies downward force to a slider that projects through a slot in the front surface of the terminates in a roller within the compartment interior. As the slider travels downwardly, it urges the roller against the tube, causing the material to dispense through the tube orifice at the bottom. The desired quantity of dispensed fluid is determined by the extend to which the slider is moved.

In one embodiment, the dispenser further includes a hinged top to provide access to the individual compartments for refilling each as required. Preferably, the dispenser can be attached to a wall or other surface using appropriate fasteners or Velcro® hook and loop type fasteners.

The preferred embodiment of the present invention provides an organized and convenient apparatus and method for dispensing bandages, gauze and first aid cream, significantly simplifying the access and dispensing of these items in hospitals, school clinics, factories, emergency rooms, doctor's offices, ambulances, and homes.

BRIEF DESCRIPTION OF THE DRAWINGS

The foregoing and other features of the invention will be apparent from the following more particular description of the invention, as illustrated in the accompanying drawings, in which like reference characters refer to the same parts throughout the different figures. The drawings are not necessarily to scale, emphasis instead being placed upon illustrating the principles of the invention.

DETAILED DESCRIPTION OF THE INVENTION

Figure 1:
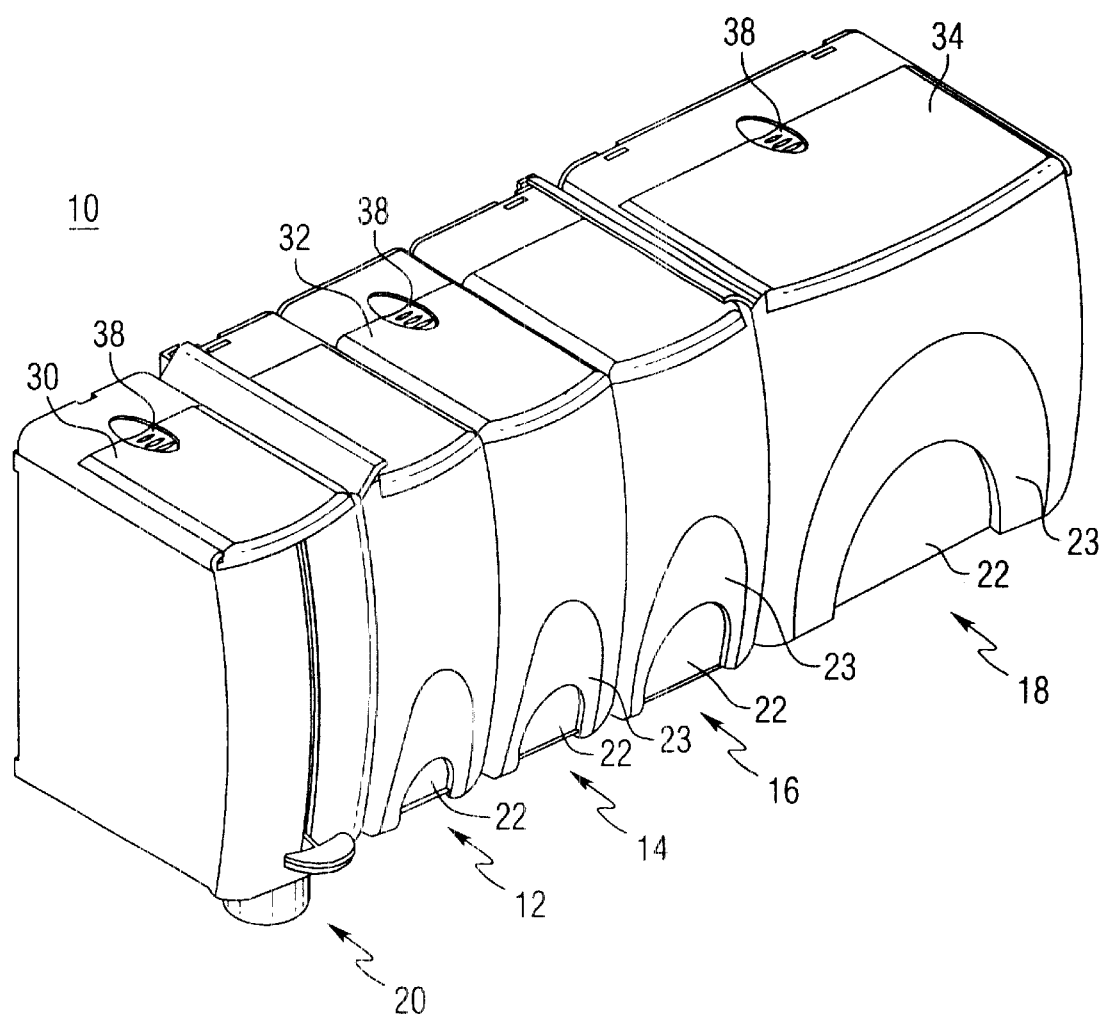
FIG. 1 is perspective view of a bandage dispenser constructed according to the teachings of the present invention.

Before describing in detail the particular bandage dispenser in accordance with the present invention, it should be observed that the present invention resides primarily in a novel combination of hardware elements related to a bandage dispenser. Accordingly, the hardware elements have been represented by conventional elements in the drawings, showing only those specific details that are pertinent to the present invention, so as not to obscure the disclosure with structural details that will be readily apparent to those skilled in the art having the benefit of the description herein.

Figure 2C:
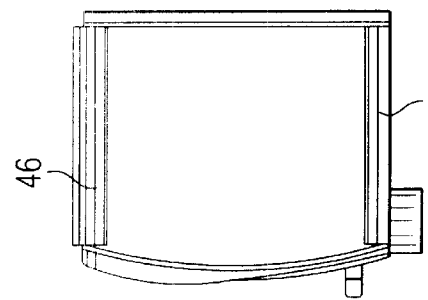
FIG. 2 is three orthographic views of the dispenser of FIG. 1.
Figure 2A:
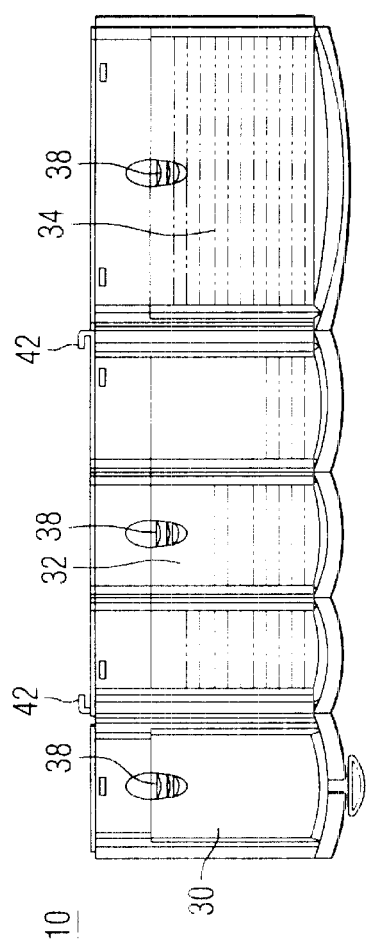
Figure 2B:
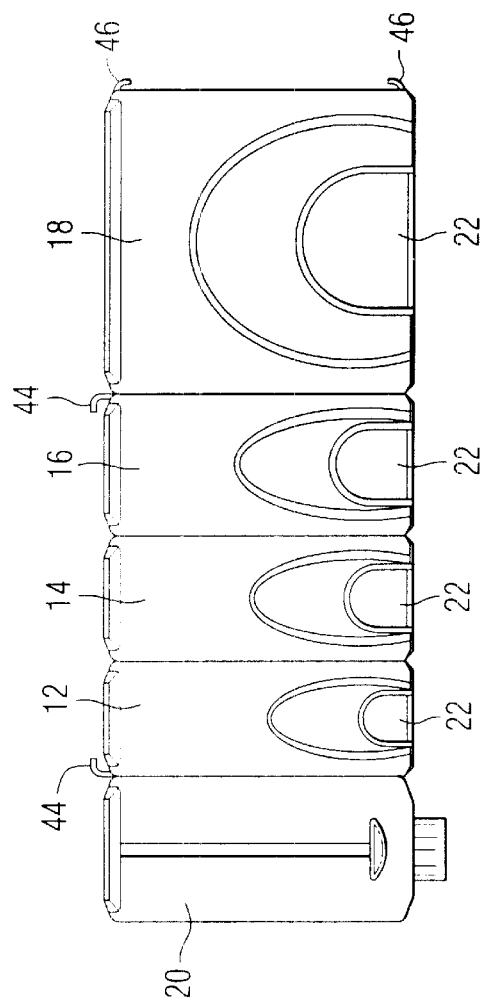

FIG. 1 is a perspective view of one embodiment of a dispenser 10 constructed according to the teachings of the present invention. FIG. 2 illustrates three orthographic views, i.e., a top view, a front view and a side view of the dispenser 10, referred to as FIGS. 2A, 2B and 2C, respectively. The FIG. 1 embodiment includes three exemplary bandage dispensing compartments 12, 14 and 16, a gauze dispensing compartment 18 and an ointment or cream dispenser 20. The dispenser 10 is conventionally constructed, for example, by injection molding of a suitable plastic material (with the dispenser body and top separately molded). Individual piece parts can also be fabricated by known plastic forming processes and assembled to create the dispenser. FIG. 1 illustrates a specific orientation of the various compartments 12, 14, 16, 18 and 20, and the description below describes mating tracks and grooves for implementing this orientation. However, the arrangement of FIG. 1 is not required, as mating grooves and tracks can be located on the various compartments to achieve a different orientation of the compartments. For instance, in another embodiment, the relative position of the gauze compartment 18 and the cream dispenser 20 can interchanged.

The bandages and gauze pads are individually wrapped and oriented vertically within the compartments 12, 14, 16 and 18. Several bandages and gauze pads are shown in phantom in the FIG. 2A top view to illustrate their placement and orientation. The front-most bandage or gauze pad is visible and accessible through an opening 22 in each of the plurality of compartments. Each opening 22 is surrounded by a concave portion 23 for receiving the user's finger or thumb during the dispensing operation. The cream dispenser 20 is closed by a cover 30, the three bandage compartments 12, 14 and 16 are closed by a single cover 32 and the gauze compartment 18 is closed by a cover 34. Each cover 30, 32 and 34 includes a finger pull 38 providing an indented area where the user can apply a horizontally directed force for sliding each of the covers 30, 32 and 34 toward the front of the dispenser 10 to access each of the compartments 12, 14, 16, 18 and 20 for refilling the compartment as required.

As shown in the FIG. 2B front view, each of the compartments 12, 14 and 16 is constructed with a different width for carrying differently-sized bandages. For example, the compartment 12 is one-half inch wide, the compartment 14 is one inch wide and the compartment 16 is two inches wide. The compartment 18 can be three inches wide for carrying three inch gauze pads. These dimensions are merely exemplary, as the dispenser 10 can be designed to fit the shape and dimensions of any commercially-available bandages. Although the compartments are designed such that the individual bandages are stacked vertically, extending from the floor surface to the cover, the dispenser 10 can also accommodate bandages of different lengths that do not extend over this entire distance.

Figure 3:
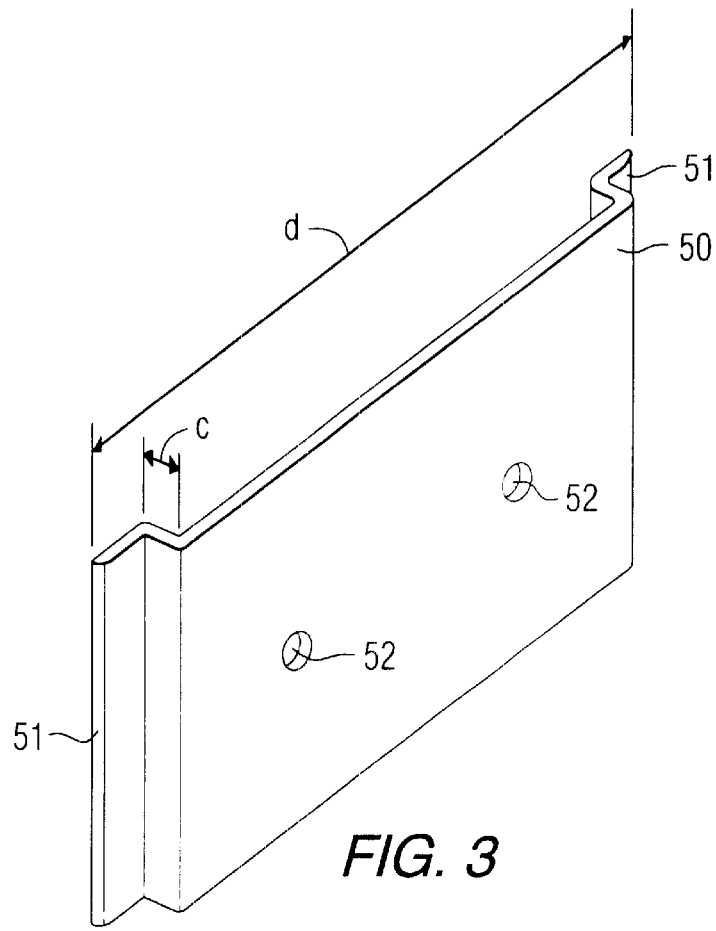
FIG. 3 is a perspective view of a mounting bracket for use with the present invention.

As further shown in FIGS. 2A and 2B, the dispenser 10 includes a pair of opposing mounting tabs 42 on the rear surface of the dispenser 10 (for rear mounting to a vertical surface) and a pair of opposing mounting tabs 44 on the top surface of the dispenser 10 (for top mounting to a horizontal surface). A mounting plate 50 having edges 51 for engaging either pair of the mounting tabs 42 or 44 is shown in FIG. 3. The distance "d" of FIG. 3 is equal to the distance between the opposing pair of mounting tabs 42 or 44, such that the edges 51 of the mounting plate 50 are slidably engaged between the mounting tabs. The mounting plate 50 can be mounted to a horizontal or vertical surface using any one of many well known fasteners passing through holes 52. The distance "c" must be greater than the length of the fastener head to ensure sufficient clearance between the mounting plate 50 and the adjacent surface of the dispenser 10.

In one embodiment, the compartments 12, 14 and 16 are formed as a single structure and include one or more mounting elements for attaching one or more gauze compartments 18 and/or one or more cream dispensers 20 to ether or both sides of the single structure. For example, FIGS. 2B and 2C illustrate upper and lower tracks 46 extending from an exposed side wall of the gauze dispenser 18, for mating with grooves (not shown) formed in the top and bottom surfaces of the cream dispenser 20 or a second gauze dispenser 18. Thus in one embodiment, each gauze dispenser 18 is formed with upper and lower tracks 46 on one side surface thereof and upper and lower grooves on the other side. The cream dispenser 20 is similarly formed. By forming the single structure comprising the compartments 12, 14 and 16 with tracks and grooves on each side thereof, the cream dispenser 20 and the gauze dispenser 18 can be mated to either side of the single structure and mated to each other by mating of the corresponding tracks and grooves to configure the dispenser 10 as desired.

Figure 4:
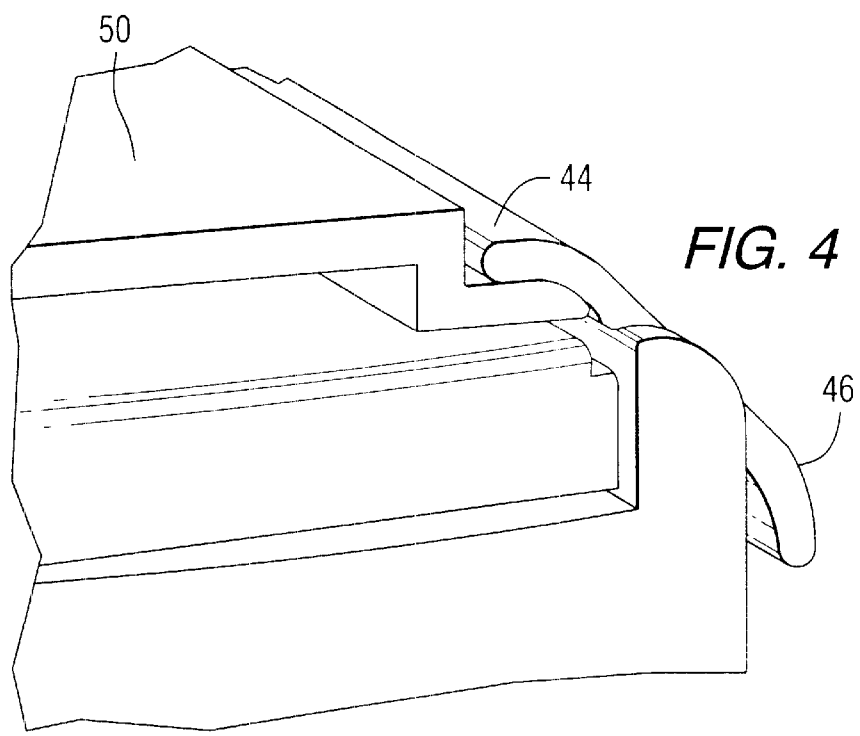
FIGS. 4 and 5 are partial close-up views of the mounting bracket of FIG. 3 and its engagement with the bandage dispenser.

FIG. 4 is close-up illustration of the mounting plate 50 slidably engaged with one of the mounting tabs 44 for mounting the dispenser 10 beneath a horizontal surface. An upper track 46 for engaging grooves in the cream dispenser 20 or the gauze dispenser 18, as discussed above, is also illustrated in FIG. 4.

Figure 5:
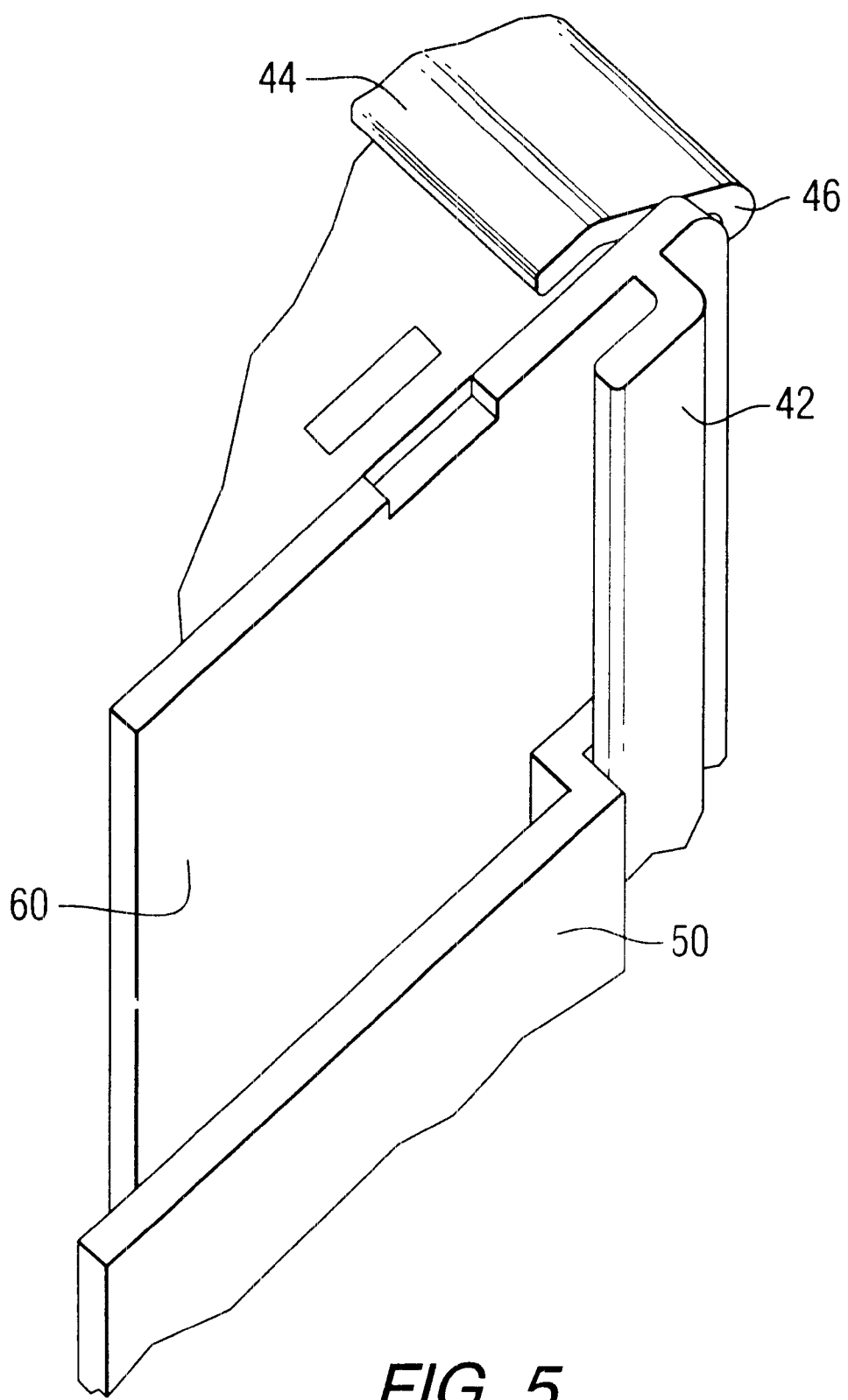

FIG. 5 is a close-up illustration of a rear-mounting configuration, where the mounting plate 50 is shown to be slidably engaged with one of the mounting tabs 42, disposed on the rear surface 60 of the dispenser 10. This configuration provides mounting against a vertical surface. Also shown in FIG. 5 is one of the mounting tabs 44 for top mounting of the dispenser 10.

Figure 6:
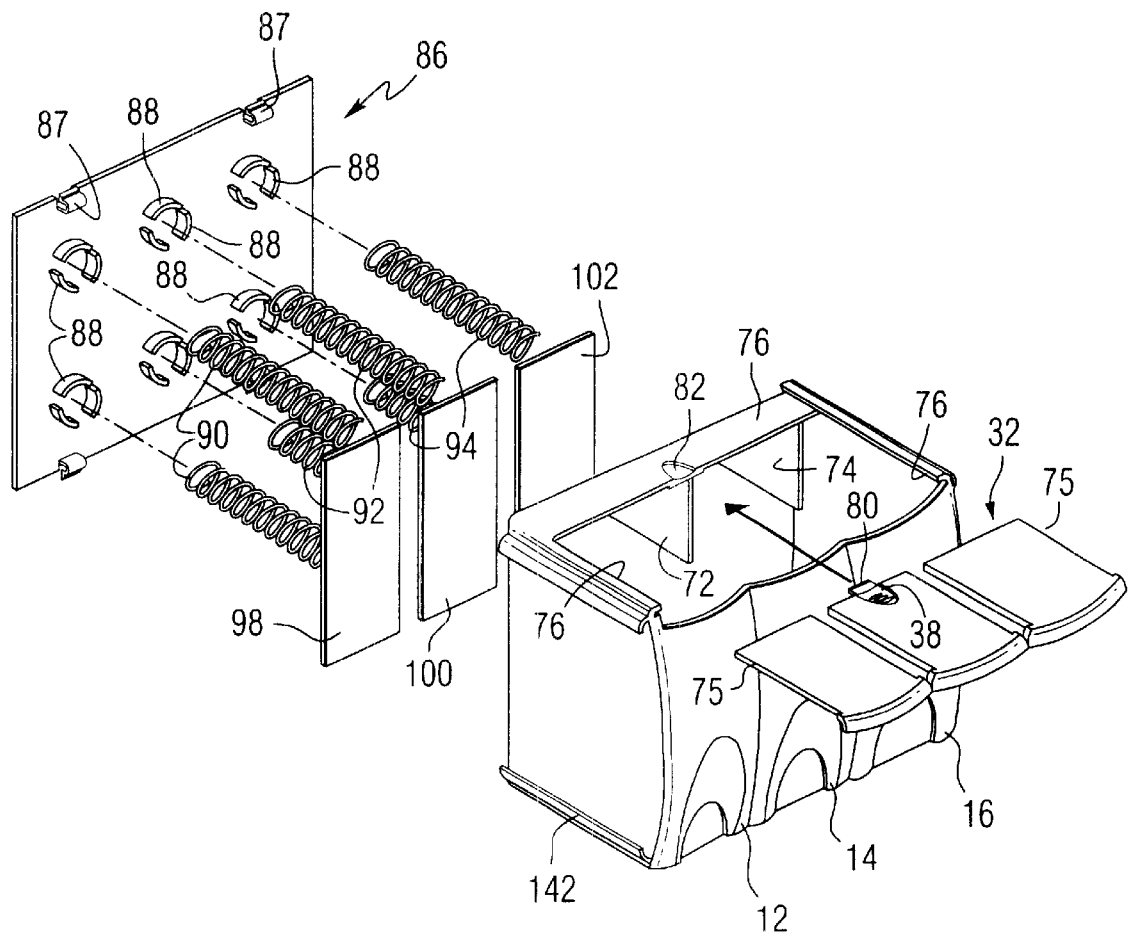
FIG. 6 is an exploded view of the bandage dispensing compartments of the present invention.

FIG. 6 illustrates certain interior components of the compartments 12, 14 and 16. Although it is not necessarily required, in the FIG. 6 embodiment, the individual compartments are not completely closed-off from the adjacent compartment. Thus surfaces 72 and 74 protrude downwardly from a top surface 76, but do not extend the full depth of the dispenser 10. As shown, three different-sized bandages can be accommodated within the interior space defined by the compartments 12, 14 and 16, as subdivided by the surfaces 72 and 74. Additional compartments can be added to the dispenser 10 to accommodate additional and differently sized bandages.

The cover 32 includes the previously mentioned finger pull 38 and a tab 80 for engaging a notch 82 thereby fixedly securing the cover 32 in place. Parallel edges 75 of the cover 32 slidably mate with opposingly parallel tracks 76. When it is desired to remove the cover 32 for loading bandages into one or more of the compartments 12, 14 or 16, the application of a downward force on the finger pull 38 releases the tab 80 form the mating notch 82, allowing the cover 32 to slide out from above the compartments 12, 14 and 16, as the edges 75 slides out from the tracks 76.

A back panel 86 forming the rear surface of the compartments 12, 14 and 16, as shown in FIG. 6, is attached thereto by tabs 87 engaging corresponding recesses (not shown in FIG. 6) in the top and bottom surfaces of the compartments 12, 14 and 16. The back panel 86 further includes a plurality of capture members 88 for engaging the rear end of the springs 90, 92 and 94. In the FIG. 6 embodiment a group of three capture members 88 engage a single spring, although the use of three capture members is not necessarily required. The rear surface of the backing plate 98 also includes capture members for engaging the front end of the springs 90. Thus the springs 90 exert a force between the back panel 86 and the backing plate 98, which in turn supplies a forwardly directed force against the row of bandages in the compartment 12. Similarly, the rear ends of the springs 92 are captured by capture members 88 and the front ends thereof are restrained by capture members on the rear surface (not shown in FIG. 6) of the backing plate 100 to exert a forwardly directed force against the bandages in the compartment 14. The rear ends of the springs 94 are also restrained by capture members 88 and the front ends by capture members the rear surface of a backing plate 102 (not shown in FIG. 6). Thus the springs 94 exert a force urging the bandages in the compartment 16 against the front surface thereof. The backing plates 98, 100 and 102 can be sized based on the size of their respective compartments 12, 14 and 16, or alternatively, can be formed of a uniform size.

In another embodiment, the back panel 86 is strengthened by the inclusion of a plurality of intersecting or parallel rib members, not shown in FIG. 6. In yet another embodiment, each compartment 12, 14 and 16 utilizes only a single spring to urge the respective backing plate 98, 100 or 102 against the row of bandages. In one further embodiment, the top spring of the two vertically spaced-apart springs of FIG. 6 supplies a smaller bias force than the bottom spring.

Figure 7:
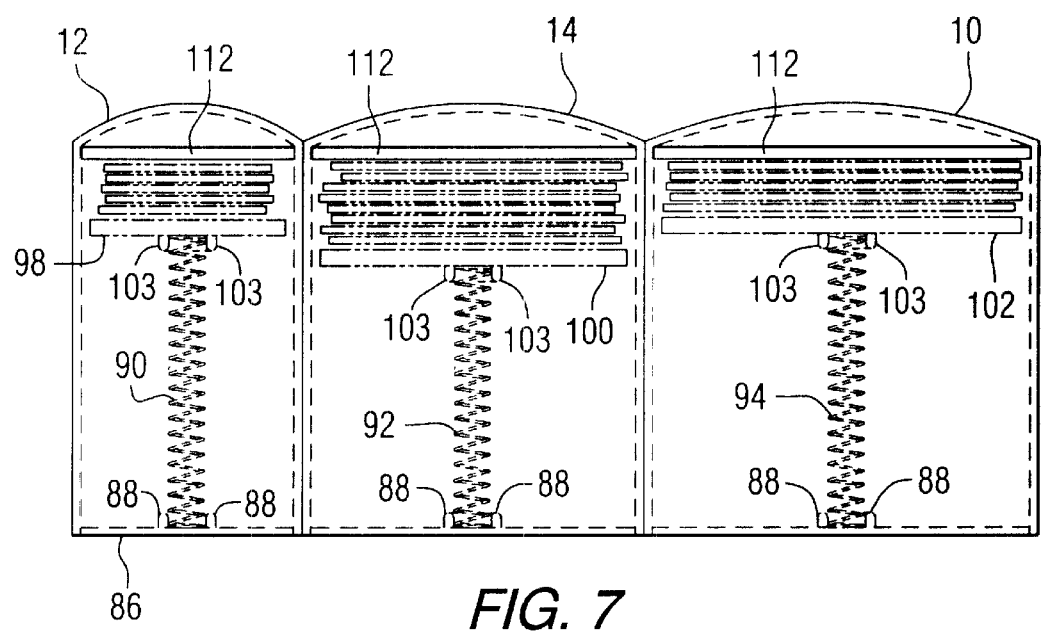
FIG. 7 is an bottom view of a dispenser constructed according to the teachings of the present invention.

FIG. 7 is a bottom view of the compartments 12, 14 and 16, showing several of the previously discussed components within the interior in phantom. In particular, FIG. 7 shows bottom slots 112 through which the bandages are dispensed by the application of a downwardly directed force through the arcuate openings 22. The capture members 103 on the rear surface of the backing plates 98, 100 and 102 as described in conjunction with FIG. 6 above are also shown in FIG. 7.

Figure 8:
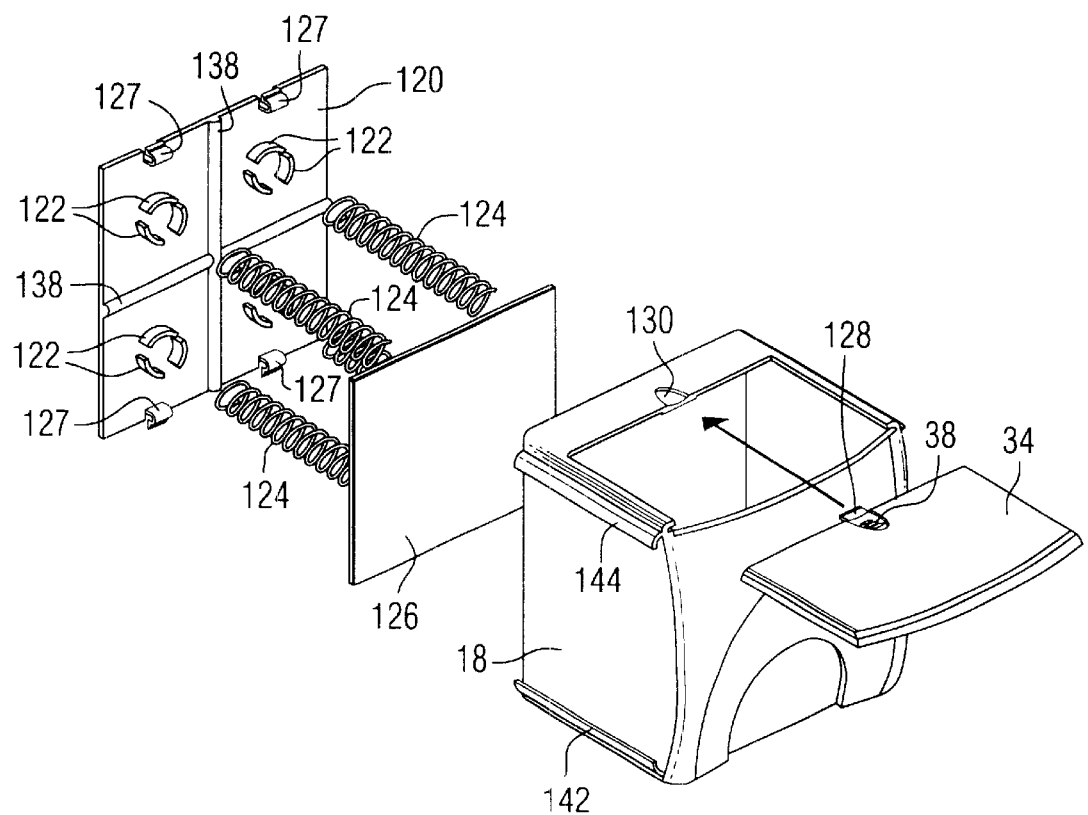
FIG. 8 is an exploded view of the gauze dispensing compartment.

FIG. 8 is an exploded view of the components of the gauze compartment 18. A back panel 120 includes a plurality of capture members 122 for holding the rear end of springs 124 in place against the back panel 120. The springs 124 urge against a backing plate 126, which in turn applies a forwardly directly force to the gauze pads within the compartment 18. The front end of the springs 124 are held in place against the backing plate 126 by engaging rearwardly facing capture members not shown in FIG. 8. Although four springs 124 are illustrated in FIG. 8, this number is not necessarily required. The back panel 120 further includes a plurality of tabs 127 for engaging corresponding recesses (not shown in FIG. 8) in the top and bottom surfaces of the compartment 18. The cover 34 includes the finger pull 38 and a tab 128 for engaging a notch 130 to hold the cover 34 in place over the compartment 18. In another embodiment, the back panel 120 further includes a plurality of parallel or intersecting rib members 138 to provide additional structural support.

To attach the gauze compartment 18 to the bandage compartments 12, 14 and 16, the former includes a pair of parallel spaced-apart tracks 142 and 144 for engaging grooves in the bandage compartment 16 such that the gauze compartment 18 is affixed to the right side of the assembly of the bandage compartments 12, 14 and 16, as illustrated in FIG. 2B. In another embodiment, similar tracks on the right side of the gauze compartment 18 (not shown in FIG. 8) provide attachment to the bandage compartment 12, such that the gauze compartment 18 is oriented to the left side of the assembly of bandage compartments 12, 14 and 16.

Figure 9:
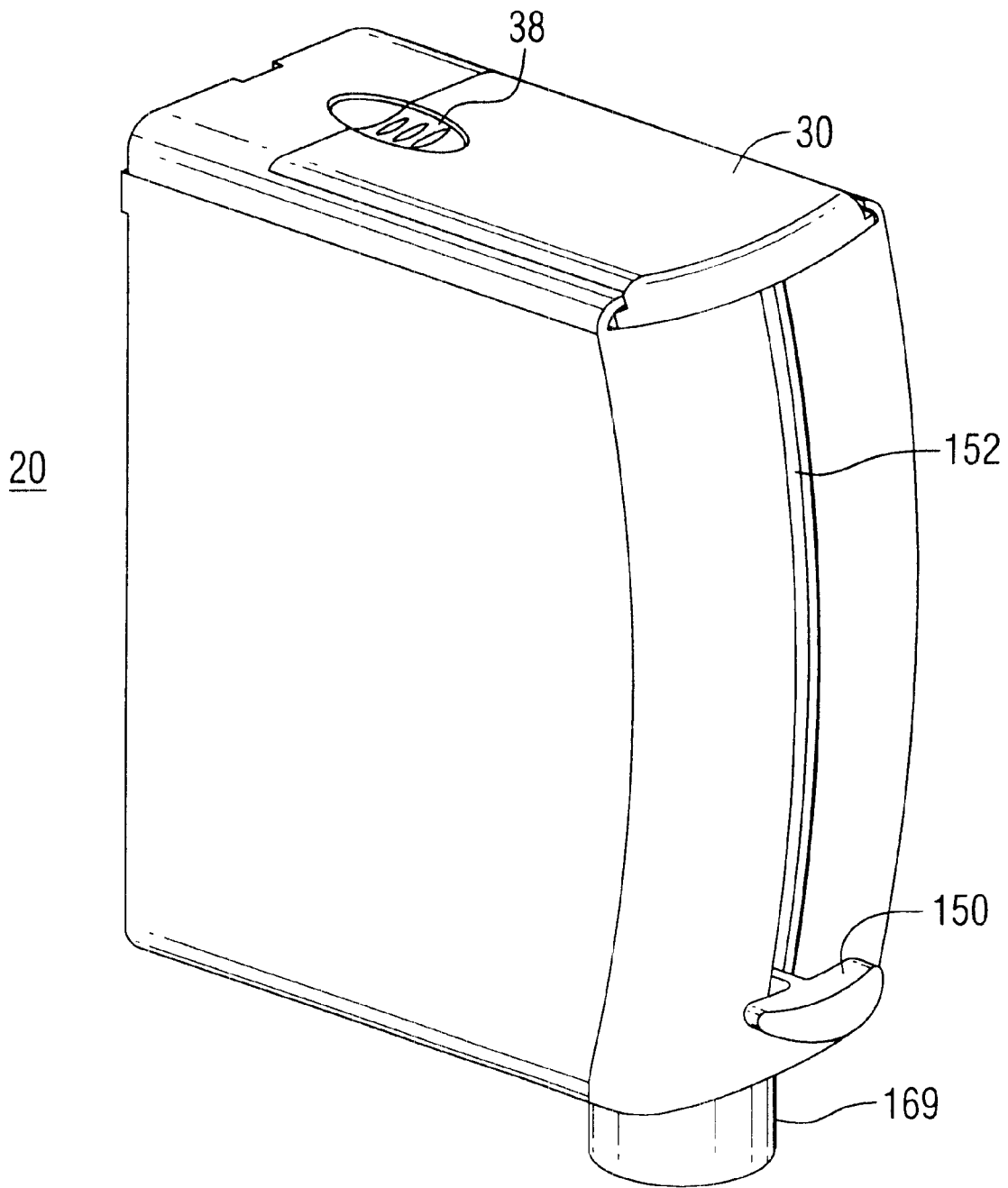
FIGS. 9, 10 and 11 show several views of the cream dispenser of the present invention.

FIG. 9 is a perspective view of the cream dispenser 20. Movement of a slider 150 within a slot 152 exerts a horizontally directed dispensing force against a vertically oriented ointment or cream tube enclosed within the cream dispenser 20. The cream dispenser 20 further comprises tracks, similar to the tracks 142 and 144 of the gauze dispenser 18, located on the side thereof hidden from view in FIG. 9. These tracks mate with grooves on the left side of the compartment 12, for forming an assembly as illustrated in FIG. 1.

Figure 10:
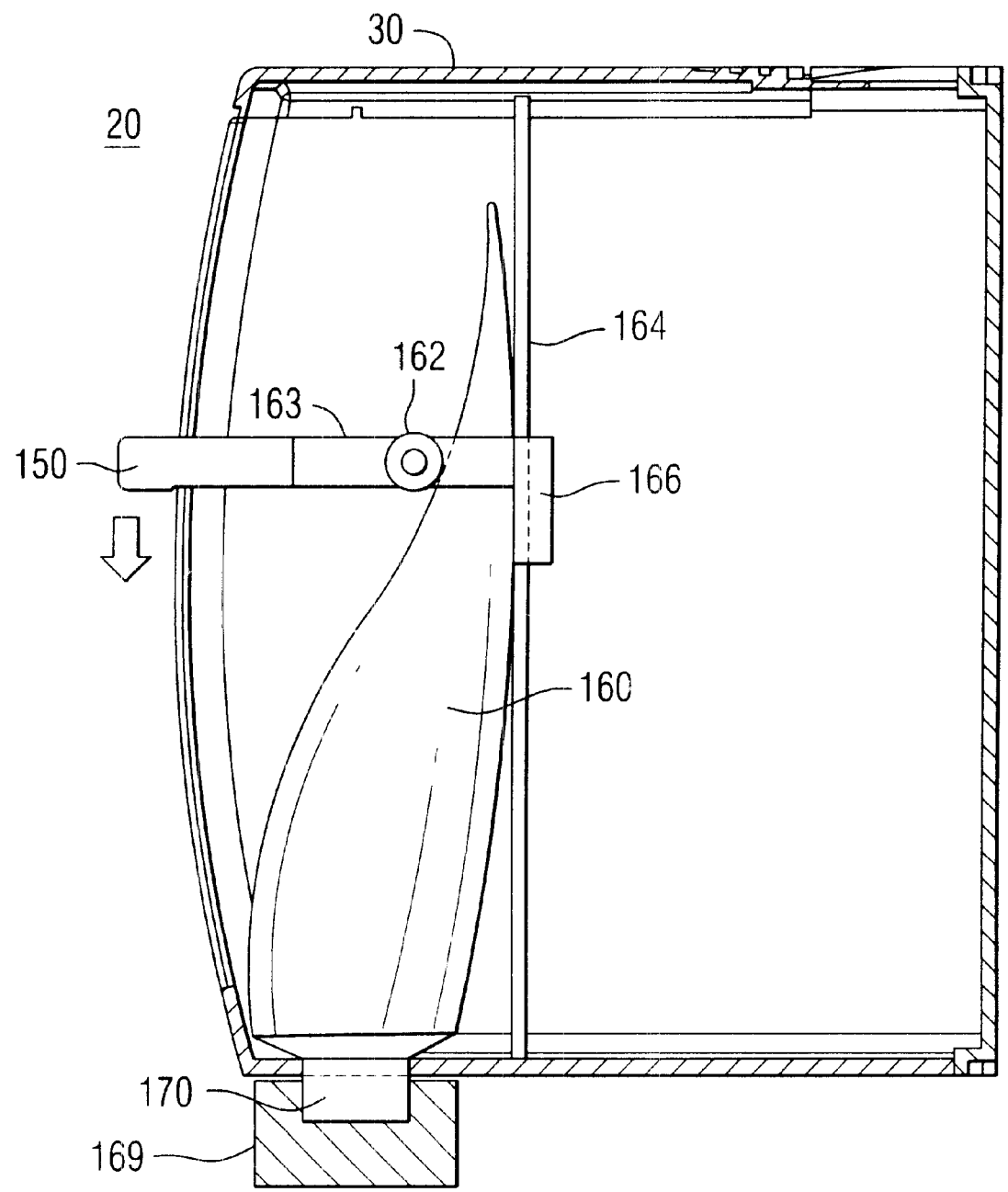

Turning to FIG. 10 the cream tube is identified by a reference character 160. A roller or pin 162, disposed between opposing legs 163 of the slider 150, applies the substantially horizontally directed squeezing force against the tube 160, which is constrained from horizontal movement by the vertical backing plate 164. Sliding guides 166, located on opposing ends of the slider 150, slide vertically along opposing vertical edges of the vertical backing plate 164 and vertical tracks in the interior surface side walls of the cream dispenser 20, thereby retaining the slider 150 in a substantially horizontal orientation as the slider 150 is moved vertically to dispense material from the tube 160. When not in use, the tube 160 is closed by a cap 169 mated to an outlet orifice 170, for instance, by a threaded or friction connection.

Figure 11:
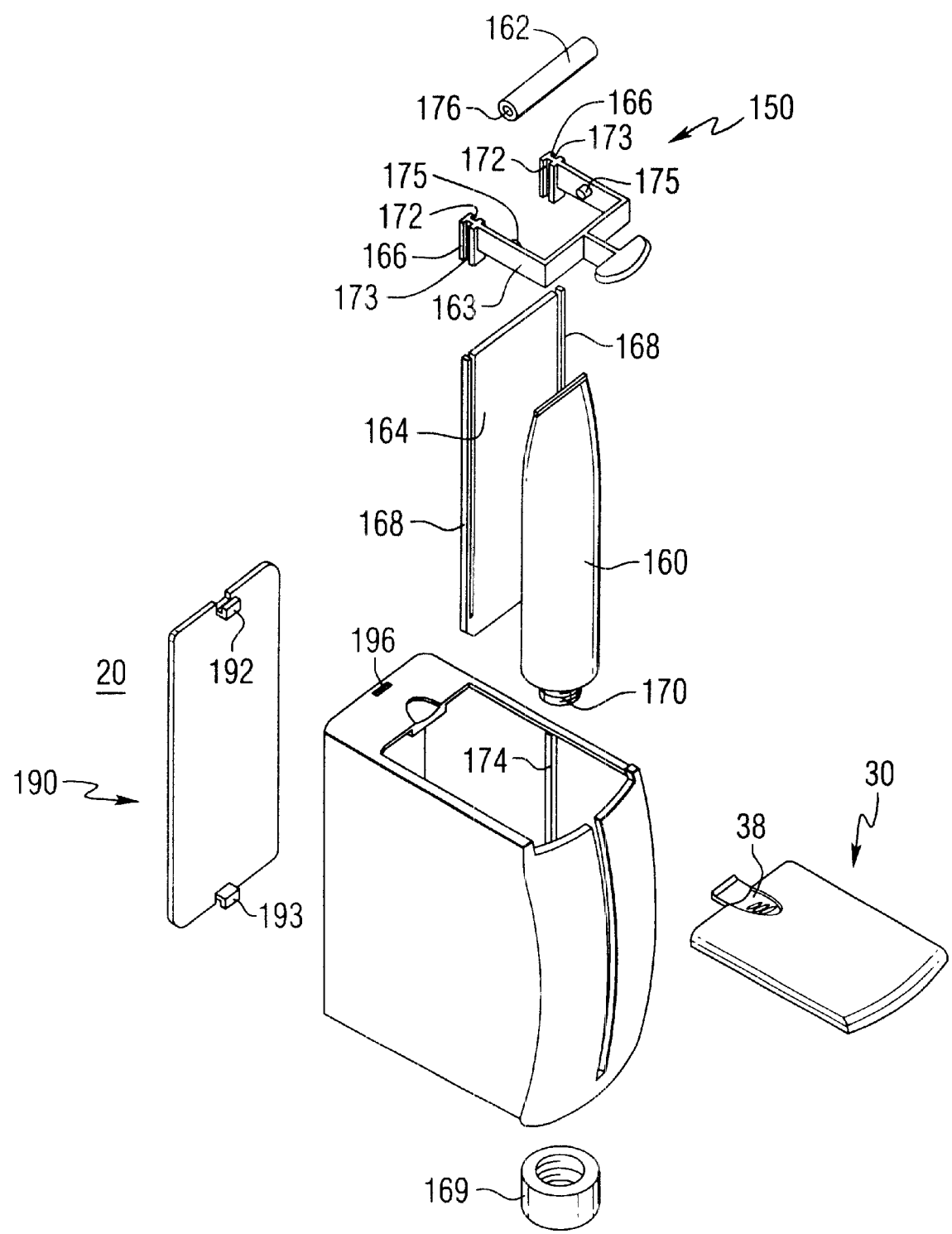

FIG. 11 illustrates the components of the cream dispenser 20 in an exploded view. As shown, the slider 150 is a U-shaped member with the sliding guides 166 disposed at the end of each leg 163. Each sliding guide 166 includes an inner-facing groove 172 for engaging opposing vertical edges 168 of the backing plate 164. Each sliding guide further includes an outer-facing groove 173 for engaging vertical tracks 174 on the side interior surfaces of the cream dispenser 20. Thus the application of an upward or a downward force vertically displaces the slider 150. Protrusions 175 located intermediate each leg 163 engage and secure in place the roller 162. The diameter of the protrusions 175 is slightly less than the diameter of a cylindrical hole 176 within the roller 162, such that roller 162 is rotatable relative to the slider 150 by the application of a downwardly directed force on the slider 150, thereby applying a substantially horizontal force against the tube 160. Although not shown in FIG. 11, a plurality vertical tracks 174 enable adjustment of the position of the of backing plate 164 as appropriate to accommodate various tube sizes.

The cream dispenser 20 further comprises a back panel 190, including an upper tab 192 for engaging a complementary recess 196 in the top surface of the cream dispenser 20, and a lower tab 197 for engaging a complementary recess in the bottom surface of the cream dispenser 20, but not shown in FIG. 11.

Figure 12:
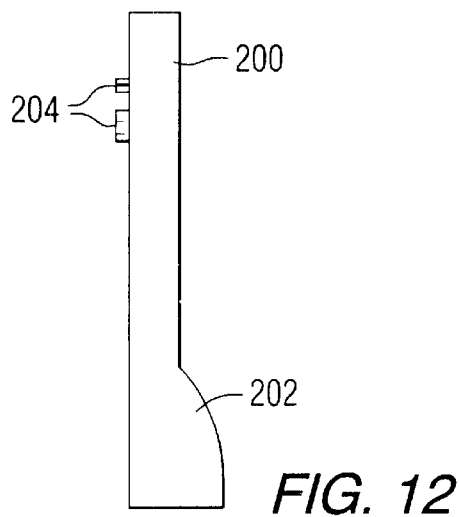
FIG. 12 illustrates one embodiment for the backing plate of the dispenser of FIG. 1.

FIG. 12 illustrates a side view of one embodiment for the backing plates 98, 100 and 102 for the bandage dispensing compartments 12, 14 and 16 and also the backing plate 126 for the gauze dispensing compartment 18. The thickness of the backing plate 200 of FIG. 12 is slightly thickened in a region 202 for urging the bottom portion of the bandages and gauze outwardly to improve the dispensing mechanism. Capture members 204 are also illustrated as grasping fingers 204 for engaging the springs 90, 92, 94 and 124 as described above.

Figure 13:
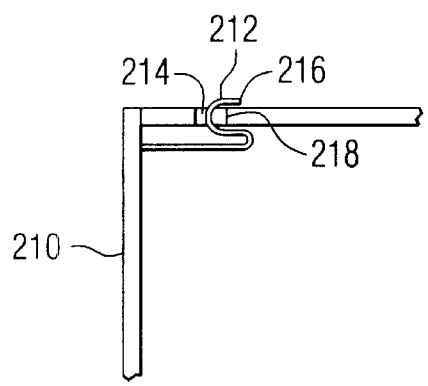
FIG. 13 illustrates one embodiment for securing the back panel of the dispenser of FIG. 1.

FIG. 13 illustrates a side view of one embodiment of a portion of a back panel 210 suitable for use as the back panel 86 of the compartments 12, 14 and 16 and as the back panel 120 of the gauze compartment 18. The back panel 210 includes a flexible tab member 212 for engaging an opening 214 in the corresponding mating surface, which as applied to the compartments 12, 14 and 16 and the gauze compartment 18 comprises the rear top surfaces thereof. To release the two mated surfaces, an edge 216 of the tab member 212 is urged toward the back panel 210 until the edge 216 clears the edge 218 of the opening 214, thereby allowing the tab 212 to pass through the opening 214. Similarly constructed flexible tabs can be located along both the top and bottom edges of the back panels 86 and 120.

Figure 14:
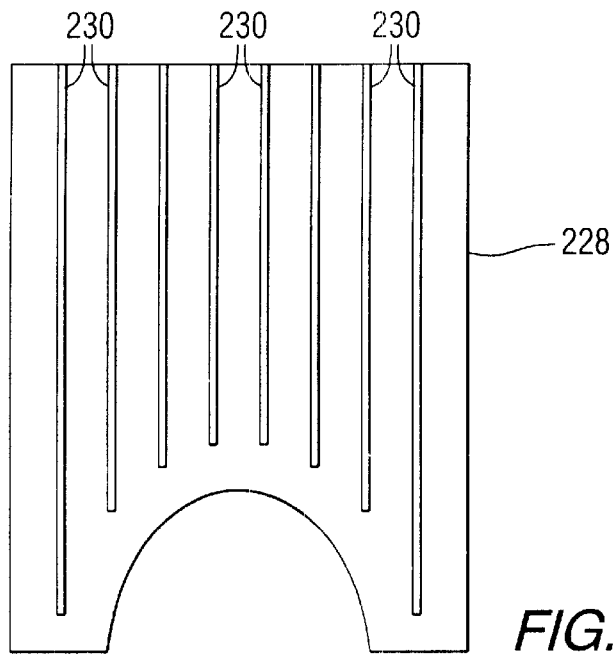
FIGS. 14 and 15 illustrate one embodiment for the front surface of the dispenser of FIG. 1.
Figure 15:
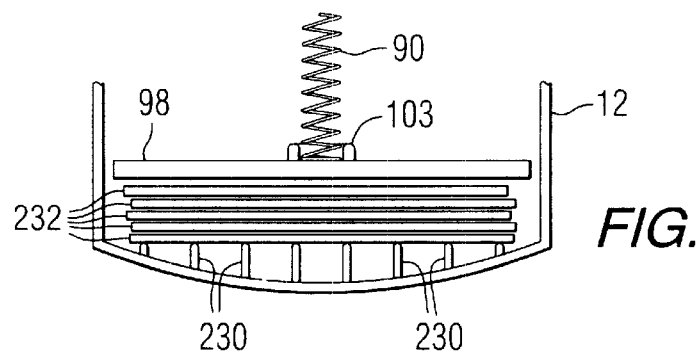

FIG. 14 illustrates the interior surface of one embodiment of a front surface 228 for one of the bandage dispensing compartments 12, 14 or 16 or the front surface of the gauze dispensing compartment 18. The front surface 228 includes a plurality of vertical ribs 230 for urging the bandages or gauze slightly away from the front surface 228 and thus improving the dispensing process. A top view of FIG. 15 further illustrates this feature for the bandage compartment 12, including the backing plate 98 and a plurality of bandages 232 stored therein.

Figure 16:
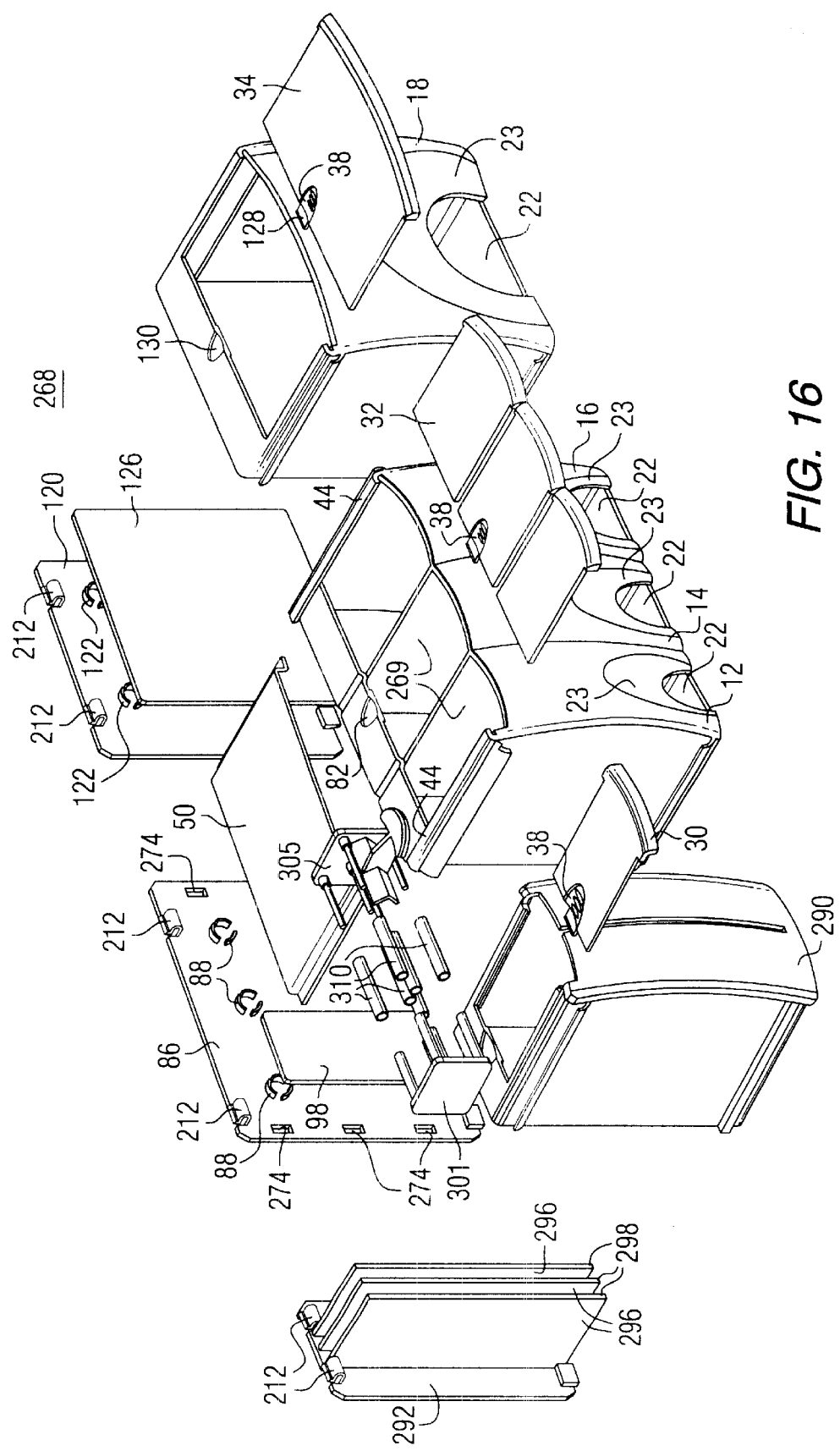
FIGS. 16 illustrates an exploded view of another embodiment of the dispenser of the present invention.

FIG. 16 is an exploded view of a dispenser 268 having several elements in common with the dispenser 10, as depicted by the common reference characters. However, in the FIG. 16 embodiment, the surfaces 72 and 74 are replaced with walls 269 for separating the compartments 12 and 14 and the compartments 14 and 16, respectively. The dispenser 268 further comprises the tab members 212 illustrated in FIG. 13. The back panel 86 further includes alignment slots 274 for engaging alignment tabs (not shown in FIG. 16) in the side walls of the compartments 12 and 16 to properly align the back panel 86 with its mating surfaces.

Figure 17:
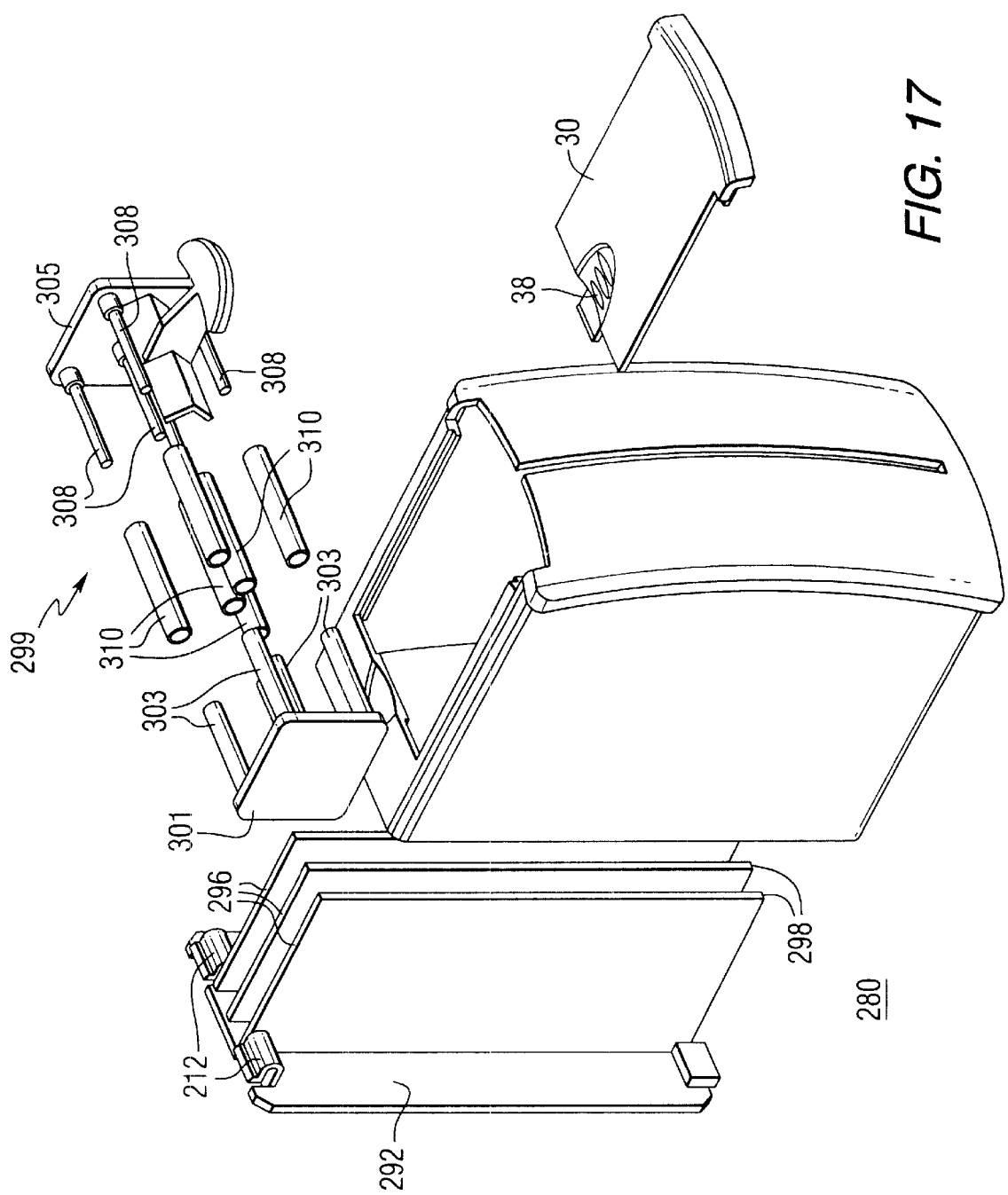
FIGS. 17 and 18 are illustrations of another embodiment of the cream dispenser of the present invention.
Figure 18:
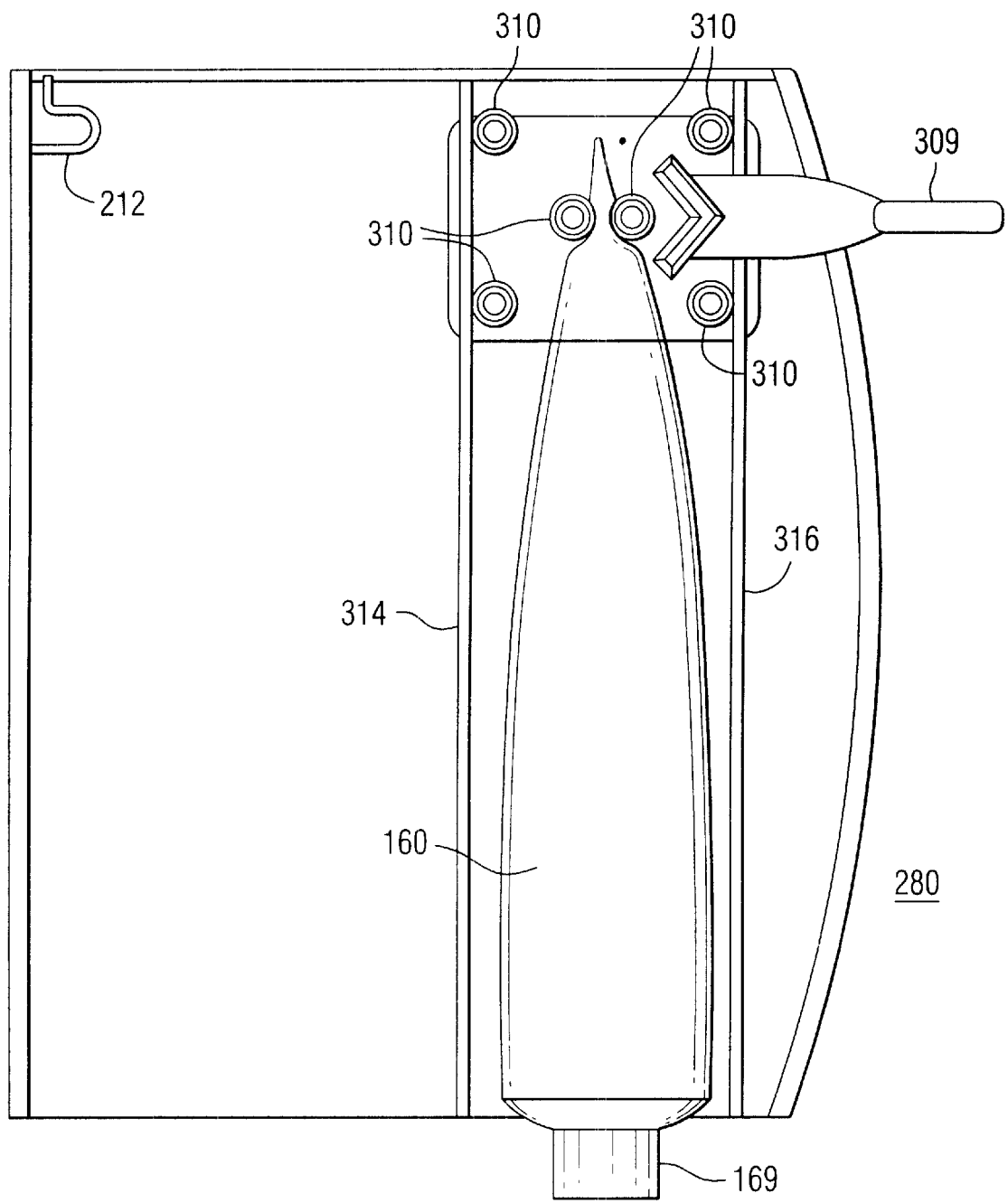

The cream dispenser 290 of FIG. 16 depicts an alternative embodiment, including several of the same elements as described in conjunction with the cream dispenser 20. The cream dispenser 290 is also illustrated in FIGS. 17 and 18. A back panel 292 has three (in this embodiment) extended members 296, each having an edge 298 for urging against the rear-facing surface of the tube 160. The cream dispenser 290 further comprises a slider 299, including a left member 301 having a plurality of protruding tubes 303. A right member 305 includes a plurality of protruding rods 308 for engaging the bore within each of the tubes 303. A slider handle 309 is also affixed to the right member 305. One of a like plurality of rollers 310 is rotatably carried by each one of the plurality of tubes 303. FIG. 18 illustrates the components in a side view, showing the spatial relationship between the several elements of the slider 299 and the tube 160. As can also be seen, the two rear-facing rollers 310 contact a panel 314 and ride along the inner surface of the panel 314 as the slider handle 309 is urged downwardly to dispense cream from the tube 160. The two inner tubes 310 are disposed on opposite sides of the tube 160 for applying a squeezing force therebetween as the slider handle 309 is urged downwardly. The front-facing tubes 310 contact a panel 316 and ride along the inner surface of the panel 316 as the slider handle 309 is urged downwardly. As a result of the arrangement of the tubes 310 with respect to the panels 314 and 316 and the tube 160, the slider 299 is held in an approximately horizontal position as the squeezing force is applied to the tube 160.

While the invention has been described with reference to preferred embodiments, it will be understood by those skilled in the art that various changes may be made and equivalent elements may be substituted for elements thereof without departing from the scope of the present invention. The scope of the present invention further includes any combination of the elements from the various embodiments set forth herein. In addition, modifications may be made to adapt a particular situation to the teachings of the present invention without departing from its essential scope thereof. For example, different sized and shaped bandages than those discussed herein can be accommodated by appropriate modifications to the teachings of the present invention. Therefore, it is intended that the invention not be limited to the particular embodiment disclosed as the best mode contemplated for carrying out this invention, but that the invention will include all embodiments falling within the scope of the appended claims.

What is claimed is:

1. A dispenser for dispensing individually-packaged injury dressings, comprising:

a plurality of adjacent compartments, each having a front surface, a rear surface and a bottom surface, wherein each compartment is sized to accept a plurality of similarly-sized injury dressings;

wherein the front surface of each compartment includes an opening proximate the bottom surface thereof;

wherein the bottom surface of each compartment includes a slot below the opening therein;

wherein similarly-sized injury dressings are disposed within each compartment between the front and the rear surfaces thereof;

a plurality of force-imparting members, wherein at least one of said plurality of force-imparting members is disposed between the rear-most injury dressing and the rear surface of each compartment, and wherein each force-imparting member exerts a force urging the injury dressings toward the front surface of the compartment, wherein the forward-most injury dressing is dispensable through the slot by the application of a downwardly-directed force against the forward-most injury dressing through the opening to dispense the forward-most injury dressing from the slot of each compartment.

2. The dispenser of claim 1 further comprising a plurality of vertically disposed members defining the width of each compartment, wherein each one of said plurality of vertically disposed members is positioned to partition adjacent ones of the plurality of compartments.

3. The dispenser of claim 1 further comprising a plurality of backing plates equal in number to the plurality of compartments, wherein one backing plate of said plurality of backing plates is fitted within each compartment, and wherein the similarly-sized injury dressings are disposed within each compartment between the front surface and said backing plate, and wherein the force-imparting member exerts a force between the rear surface and said backing plate of each compartment.

4. The dispenser of claim 1 wherein each compartment has a removable top surface for gaining access to the compartment interior for loading injury dressings into the compartment.

5. The dispenser of claim 4 wherein a single top surface covers a plurality of adjacent compartments.

6. The dispenser of claim 4 wherein the dispenser further comprises parallel opposing tracks along the top surface thereof, for slidably engaging the removable top surface.

7. The dispenser of claim 6 wherein the top surface further comprises a tab member, and wherein the rear surface of the dispenser further comprises a notch member for removably engaging said tab member.

8. The dispenser of claim 1 wherein the opening of each compartment has an arcuate shape.

9. The dispenser of claim 8 further comprising a depressed concave area in the front surface proximate each arcuately shaped opening.

10. The dispenser of claim 1 wherein each one of the plurality of force-imparting members comprises a helical spring.

11. The dispenser of claim 1 further comprising a surface mounting plate and a top surface including parallel opposing horizontal tracks, wherein said surface mounting plate is mountable upon a horizontal surface, and wherein opposing edges of said surface mounting plate slidably engage said horizontal tracks for affixing the dispenser to the horizontal surface.

12. The dispenser of claim 1 further comprising a surface mounting plate and parallel opposing vertical tracks on the rear surface thereof, wherein said surface mounting plate is mountable on a vertical surface, and wherein opposing edges of said surface mounting plate slidably engage said vertical tracks for affixing the dispenser to the vertical surface.

13. The dispenser of claim 1 wherein the injury dressings comprise bandages.

14. The dispenser of claim 1 wherein the injury dressings are vertically oriented within each compartment.

15. The dispenser of claim 1 further comprising an ointment-dispensing compartment for dispensing material from a vertically oriented flexible tubular enclosure contained within said ointment-dispensing compartment in an upside-down orientation, and wherein said ointment dispensing compartment comprises a user-operated slidable member for exerting a squeezing force against the tubular enclosure, such that material is dispensed from the tubular enclosure through the bottom directed orifice thereof.

16. The dispenser of claim 15 wherein the ointment-dispensing compartment further comprises a pair of rollers disposed on either side of the tubular enclosure and rotatably attached to the slider member for imparting the squeezing force as the slider member is urged downwardly.

* * * * *